US005393887A

United States Patent [19]
Petit

[11] Patent Number: 5,393,887
[45] Date of Patent: * Feb. 28, 1995

[54] BISIMIDE COMPOSITIONS

[75] Inventor: Christian J. Petit, Chicopee, Mass.

[73] Assignee: Monsanto Company, St. Louis, Mo.

[ * ] Notice: The portion of the term of this patent subsequent to Apr. 12, 2011 has been disclaimed.

[21] Appl. No.: 130,946

[22] Filed: Oct. 4, 1993

[51] Int. Cl.$^6$ ............ C07D 209/02; C07D 209/34; C07D 207/448

[52] U.S. Cl. ............ 548/465; 548/486; 548/521

[58] Field of Search ............ 548/521, 486, 465

[56] References Cited

U.S. PATENT DOCUMENTS

| | | | |
|---|---|---|---|
| 4,125,535 | 11/1978 | Wolford | 260/326 N |
| 4,130,600 | 12/1978 | Zahir et al. | 260/820 P |
| 4,876,325 | 10/1989 | Olson et al. | 528/170 |
| 4,883,843 | 11/1989 | Taniuchi et al. | 525/327.6 |
| 4,985,478 | 1/1991 | Kameyama et al. | 523/219 |
| 5,004,775 | 4/1991 | Olson et al. | 524/371 |
| 5,034,503 | 7/1991 | Camberlin | 528/322 |

*Primary Examiner*—Joseph L. Schoffer
*Assistant Examiner*—Wu C. Cheng
*Attorney, Agent, or Firm*—Michael J. Murphy; Mark F. Wachter

[57] ABSTRACT

A mixed bisimide having the formula:

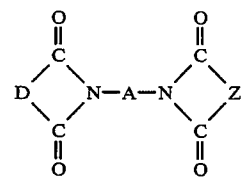

wherein D, A and Z are as defined in the specification, produced by reacting a diamine with an ethylenically unsaturated dicarboxylic acid anhydride and a halogenated compound containing an anhydride group and aromatic or bicyclo groups to form a bisamic acid composition and then dehydrating such composition to ring close the end groups. The halogenated end groups (Z) of the mixed bisimide component render the bisimide reaction product of the ring closing reaction flame retardant.

2 Claims, No Drawings

BISIMIDE COMPOSITIONS

BACKGROUND OF THE INVENTION

This invention relates to bisimide compositions and more particularly to such compositions modified for flame-retardancy, and to a process for producing same.

Bisimide compositions containing unsaturated reactive groups are known as components of thermoset resins useful as adhesives in laminates for the electronics industry such as printed wiring boards, thermoset molding components, honeycomb structures and the like. Typically the bisimide composition is chain extended or partially polymerized, usually with one or more coreactants, to form a prepolymer, then applied to components of the laminate and cured at elevated temperature and pressure, sometimes with additional coreactants and usually in the presence of a crosslinking agent. The resulting thermoset structure resists deterioration at high use temperatures on the order of about 250°–300° C.

Flame-retardance (sometimes herein called "flame resistance") is desirable in commercial applications of these thermoset resins. As used herein, flame retardance means capability of passing Underwriters Laboratories Inc. Standard Test for Flammability of Plastic Materials for Parts in Devices and Appliances, passing Material Classification UL 94V-1, preferably V-0 thereof. In the past flame retardance was achieved by adding halogen compounds to the partially polymerized prepolymer before final elevated temperature curing. See, for example, U.S. Pat. No. 5,004,775, issued Apr. 2, 1991, where octabromodiphenyl oxide is used. Also used were halogen compounds which copolymerize with the bisimide compositions during formation of the prepolymer before curing. See, for example, U.S. Pat. No. 4,876,325, issued Oct. 24, 1989, Example 2 where brominated bisphenol A is used. Unfortunately, during elevated temperature curing, such external flame-retardant additives volatilize to cause blistering and undesirable layer separation of the laminated board and loss of flame resistance.

It would be desirable to improve the flame-retardant performance of such bisimide compositions in these high temperature applications.

SUMMARY OF THE INVENTION

Now, improvements have been made to alleviate the aforementioned performance shortcomings of the prior art.

Accordingly, a principal object of this invention is to provide inherently flame-retardant bisimide compositions wherein halogen atoms are permanently, internally chemically bound into bisimide molecules, which compositions contain unsaturation sites available to chain extend and cure in conventional manner to form a flame-retardant, blister-resistant, thermoset product.

Another object of this invention is to provide a process for preparing such inherently flame resistant bisimide compositions.

Other objects of this invention will in part be obvious and will in part appear from the following detailed description and claims.

These and other objects are accomplished by modifying the known process for forming bisimide compositions by replacing a sufficient amount of ethylenically unsaturated dicarboxylic acid anhydride (e.g. maleic anhydride) (hereinafter "EUDAA") reacting with diamine in forming bisamic acid intermediate, with a halogenated anhydride-group-containing compound so as to provide about 5 to 15 weight percent halogen in the mixed bisamic acid intermediate compound and the subsequent ring-closed mixed bisimide compound. After dehydrating ring-closing, the bisimide composition is flame-retardant from the presence of an effective amount of about 5 to 15, preferably 7 to 10 weight % of halogen provided by the halogenated compound. The halogenated end-groups are saturated or free of non-benzenoid unsaturation and will not react further during chain extending and curing, yet the bulk of the end groups contain unsaturated carbon-carbon double bonds which will further react.

Reflecting the foregoing is an intermediate bisamic acid composition comprising the reaction product of i) diamine ii) ethylenically unsaturated dicarboxylic acid anhydride and iii) a halogenated compound containing a) aromatic or bicyclo and b) anhydride groups, the molar ratio of iii/ii being no more and preferably less than 1:1.

Also a mixed bisimide compound having the formula:

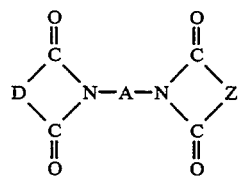

where D is a divalent radical containing a polymerizable carbon-carbon double bond, A is an organic divalent linking group and Z is a halogenated divalent radical containing one or more aromatic or bicyclo groups. In the above formula I, D is preferably:

where $R_1$ and $R_2$ are each H;

A is preferably:

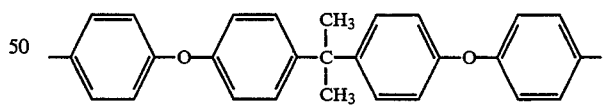

Z (defining the halogenated end groups referred to above) is preferably:

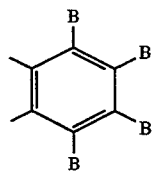

where B is Br or Cl.

Further, a flame-retardant bisimide composition comprises:

a) a bisimide having the formula:

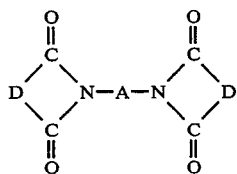

II and b) a mixed bisimide of formula I where D, A and Z are as defined above; the mole ratio of a/b being at least 1/1.

In a preferred form, the flame-retardant bisimide composition comprises a mixture of bismaleimide and mixed maleimide/tetrabromophthalimide wherein the mixture contains 7 to 10 weight % bromine.

In another aspect, a curable flame-retardant composition comprises the flame-retardant bisimide composition defined above in combination with one or more coreactants.

The process for preparing a flame-retardant bisimide composition comprises: a) reacting i) diamine with ii) a mixture of ethylenically unsaturated dicarboxylic acid anhydride and a halogenated compound containing aromatic or bicyclo groups and an anhydride group to form an intermediate bisamic acid composition, the molar ratio of the halogenated compound to the ethylenically unsaturated dicarboxylic acid anhydride being no more than 1:1; and b) dehydrating the bisamic acid composition to ring close the end groups and form a flame-retardant bisimide composition having end groups containing ethylenically unsaturated carbon-carbon bonds and groups free of non-benzenoid unsaturation containing halogen atoms and aromatic or bicyclo groups.

DETAILED DESCRIPTION OF THE INVENTION

The flame retardant bisimide compositions are prepared by modifying the generally known two step process wherein diamine and EUDAA are reacted to form bisamic acid intermediate followed by end group ring closing dehydration to form the bisimide composition. In the modified process, the flame-retardant component in the bisimide mixture is formed by including a flame retarding amount of an anhydride-group-containing halogenated compound (further described hereafter) in the initial reaction mixture. This amount is effective to provide at least a UL 94V-1 rating to laminated products made using the halogenated bisimide composition. Such amount will vary with the halogen content of the anhydride-group-containing halogenated component and usually replaces a portion of the stoichiometric amount of EUDAA required to fully react with the diamine. Considered with respect to the EUDAA, the molar ratio of the anhydride-group-containing halogenated compound to EUDAA is broadly always no more and preferably less than 1:1 and specifically is such as to produce about 5 to 15 (preferably 7 to 10) weight % chemically combined halogen in the molecules of the compositions (i.e. the intermediate bisamic acid mixture and the subsequent bisimide mixture) having the mixed end groups. The anhydride group of the halogenated compound reacts with the diamine the same as does the EUDAA to form the halogenated end groups on the bisamic acid intermediate composition. Once the anhydride group of the halogenated compound reacts with the NH$_2$ of the diamine, the ring-halogenated moiety is chemically bound as an integral part of the initial bisamic acid component and the subsequent ring-closed imide component. Since the molar amount of the anhydride-group-containing halogenated compound is not more than the EUDAA, the preponderance of end groups are the product of the diamine-EUDAA reaction. Moreover, because of the usually large quantity of EUDAA relative to the halogenated compound, only a small portion of bisamic acid molecules have mixed end groups—i.e. those containing an ethylenically unsaturated double bond on one end necessary and available for subsequent downstream chain extending and/or curing, and halogenated groups on the other end which, since without unsaturation (other than benzenoid unsaturation in certain embodiments) are "dead" and not capable of reacting further. The halogen atoms of the halogenated end groups are inherently present and therefore intimately contact all components constituting the downstream chain extended polymer mixture typically used, as above noted, as adhesive joining layers of laminates in end use products. The halogen atoms of such halogenated groups in such end use products provide inherent flame-resistance in the mixtures of the invention. The integrally chemically bound halogen atoms in the imide rings of the molecular structure are more thermally stable and resistant to migration and blistering at elevated temperatures typically encountered in manufacturing laminated printed wiring boards and end-use laminated board applications than are admixed halogenated additives.

The two step process for forming bisimides is generically described in U.S. Pat. No. 4,,460,783, issued Jul. 17, 1984, col. 3, lines 10–54, the content of which is incorporated herein by reference. In summary, and including the modification of the invention, in the first step diamine, EUDAA and anhydride-group-containing halogenated compound containing aromatic or bicyclo groups are reacted in an organic solvent at a temperature of about minus 10° to +120° C. for 0.5 to 10 hrs. to give the bisamic acid intermediate mixture. In this reaction, the molar ratio of halogenated compound to EUDAA is preferably less than 1:1. In the second step, the bisamic acid intermediate mixture is dehydrated to ring-close the bisamic acid end groups and form the flame-retardant bisimide composition.

Usable organic solvents in the first step include one or more of dimethyl formamide, dimethyl acetamide, dimethyl sulfoxide, N-methyl-pyrrolidinone, N-methyl-caprolactam, tetrahydrofuran, dioxane, acetone, diethyl ketone, methyl ethyl ketone, toluene and the like.

The bisamic acid mixture is a stable intermediate used, preferably in situ as made, as the starting material for producing flame-retardant bisimide mixtures of the invention.

Ring-closing of bisamic acid intermediate in the second step is carried out using an anhydrous substance for dehydration such as acetic anhydride, propionic anhydride, butyric anhydride and the like in the amount of 1.05 to 2.0 moles per mole of the amic acid group, in the presence of a catalyst such as nickel acetate, cobalt acetate, lithium acetate, potassium acetate, sodium acetate, calcium acetate, or the like in the amount of 0.003 to 0.05 mole per mole of the amic acid group, and in a solvent such as acetone, N-methylpyrrolidinone, toluene or the like at a temperature of 60° to 120° C. for about 0.5 to 7 hrs. Alternatively, ring-closing dehydrating can be carried out without such anhydrous substances and metal acetate catalysts using instead an acid catalyst such as methane sulfonic acid, paratoluene sulfonic acid, sulfuric acid, trifloroacetic or other strong mineral or organic acids in the amount of 0.03-0.2 mole of acid per mole of bisamic acid.

Bisimide compositions of the invention contain a halogenated mixed bisimide compound for flame-retardance of the formula I noted above where:
D is a divalent radical of the formula:

where $R_1$ and $R_2$ each and independently of each other denote a hydrogen atom or an aliphatic, cycloaliphatic or aromatic group containing 1-12 carbon atoms. Preferably $R_1$ and $R_2$ each are a hydrogen, methyl or ethyl group, in particular a hydrogen atom.

A is an organic, divalent linking group which may be an aliphatic, cycloaliphatic, aromatic or heterocyclic group and generally contains 2-40 carbon atoms; when A is an aliphatic group it preferably contains 2-6 carbon atoms; A preferably is an aromatic group, in particular a phenylene group or a group of the formula:

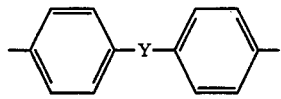

where Y denotes a —CH$_2$—, a —C(CH$_3$)$_2$—, an —O—, an —SO$_2$— or an

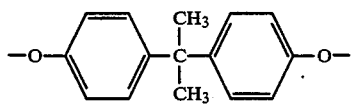

group.

The latter aromatic ether group is a particularly preferred form of Y.

Z is a halogenated divalent radical containing one or more aromatic or bicyclo groups which is derived from an anhydride-group-containing compound—i.e. one containing the

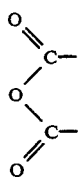

group.
Exemplary forms of the radical Z (halogen atom position based on the anhydride) include:

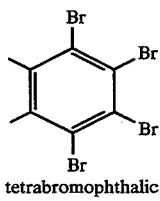
tetrabromophthalic

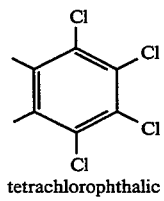
tetrachlorophthalic

-continued

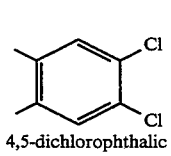
4,5-dichlorophthalic

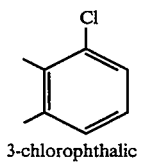
3-chlorophthalic

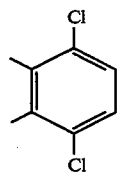
3,6-dichlorophthalic

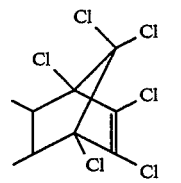
1,4,5,6,7,7-hexachloro-5-norbornene-2,3-dicarboxylic

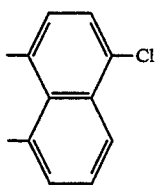
4-chloro-1,8-naphthalic

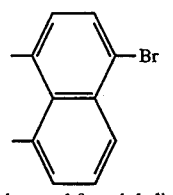
4-bromo-1,8-naphthalic

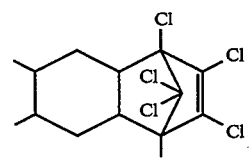
hexachlorohexahydro-1,4-methanonaphthalene-6,7-dicarboxylic

Z preferably is a tetrahalogenated (e.g. Br or Cl), phthalic group—i.e.

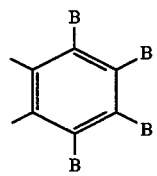

where B is Br or Cl.

The halogenated compound(s) must have the noted anhydride group for reacting with the diamine to produce end groups in the mixtures which satisfy radical Z in formula I. The number of halogen atoms (preferably bromine or chlorine) per radical Z can vary, is preferably more than one and typically at least four. Such compounds are commercially available from vendors of flame-retardant additives, such as Great Lakes Chemical Corporation of West Lafayette, Ind. or Aldrich Chemical Company of Milwaukee, Wis.

Any diamine or mixture of diamines capable after ring-closing of providing compositions of formula I, may be used. Exemplary diamines include bisaminophenoxyphenyl propane, p-methylene diamine and other such diamines including the following;
1,1-bis(4-amino-3-methylphenyl)cyclohexane
1,1-bis(4-aminophenyl)cyclohexane
1,1-bis[3-bromo-4-(4-aminophenoxy)phenylethane
1,1-bis[3-chloro-4-(4-aminophenoxy)phenylethane
1,1-bis[3-methyl-4-(4-aminophenoxy)phenylethane 1,1-bis[4-(4-aminophenoxy)phenyl]ethane
1,1-bis[4-(4-aminophenoxy)phenyl]propane
1,1,1,3,3,3-hexachloro-2,2-bis[4-(4-aminophenoxy)-
  phenyl]propane
1,1,1,3,3,3-hexafluoro-2,2-bis[4-(4-aminophenoxy)-
  phenyl]propane
1,1,1,3,3,3-hexafluoro-2,2-bis[3,5-dibromo-4-(4-amino-
  phenoxy)phenyl]propane
1,1,1,3,3,3-hexafluoro-2,2-bis[3,5-dimethyl-4-(4-amino-
  phenoxy)phenyl]propane
1,1,1,3,3,3-hexafluoro-2,2-bis[3-methyl-4-(4-amino-
  phenoxy)phenyl]propane
1,4-diaminocyclohexane
1,5-diaminonaphthalene
2,2'-bis(4-aminophenyl)propane
2,2'-bis[3-bromo-4-(4-aminophenoxy)phenyl]propane
2,2'-bis[3-chloro-4-(4-aminophenoxy)phenyl]propane
2,2'-bis[3-methyl-4-(4-aminophenoxy) phenyl]propane
2,2-bis[3-butyl-4-( 4-aminophenoxy) phenyl]propane
2,2-bis[3-ethyl-4-( 4-aminophenoxy) phenyl]propane
2,2-bis[3-isopropyl  -4-(4-aminophenoxy)phenyl]pro-
  pane
2,2-bis[3-methoxy-4-(4-aminophenoxy)phenyl]propane
2,2-bis[3-propyl-4-(4-aminophenoxy)phenyl propane
2,2-bis[3-sec.-butyl-4-(4-aminophenoxy)phenyl]propane
2,5-bis(m-aminophenyl)thiazolo(4,5-dithiazole)
2,5-bis(m-aminophenyl)-1,3,4-oxadiazole
2,5-bis(p-aminophenyl)-1,3,4-oxadiazole
2,6-diaminopyridine
3,3'-diaminodiphenylenemethylphosphine oxide
3,3-bis[4-(4-aminophenoxy)phenyl]pentane
4,4'-bis(p-aminophenyl)-2,2'-dithiazole
4,4'-di-(m-aminophenoxy)diphenylmethane
4,4'-di-(m-aminophenoxy)diphenylether
4,4'-di-(m-aminophenylsulfonyl)diphenylether
4,4'-di-(m-aminophenoxy)diphenylsulfone
4,4'-di-(m-aminophenylthioether)diphenylsulfide
4,4'-di-(m-aminophenoxy)diphenylpropane
4,4'-di-(p-aminobenzoyl)diphenylether
4,4'-di-(p-aminophenylsulfonyl)diphenylether
4,4'-di-(p-aminophenoxy)diphenyldifluoromethane
4,4'-di-(p-aminophenylthioether)diphenylsulfide
4,4'-di-(p-aminophenoxy)-diphenylmethane
4,4'-di-(p-aminophenoxy)-diphenylsulfone
4,4'-diaminoazobenzene
4,4'-diaminobenzanilide
4,4'-diaminobenzophenone
4,4'-diaminodicyclohexylmethane
4,4'-diaminodiphenylmethane
4,4'-diaminodiphenylsulfone
4,4'-diaminodiphenylenephenylamine
4,4'-diaminodiphenylenediphenylsilane
4,4'-diaminodiphenylenesulfide
4,4'-diaminodiphenylether
4,4'-diaminophenylbenzoate
4,4'-methylene-bis(2-chloroaniline)
5,5'-di(m-aminophenyl)-2,2'-bis(1,3,4-oxadiazolyl)-4,4'-
  diaminodiphenylether
6,6'-diamino-2,2'-dipyridyl
bis(4-aminophenyl)methylamine
bis(4-aminophenyl)phenylphosphine oxide
bis(4-aminophenyl)phenylmethane
bis[3-bromo-4-(4-aminophenoxy)phenyl]methane
bis[3-chloro-4-(4-aminophenoxy)phenyl]methane
diaminophenylindane
ethylenediamine
hexamethylenediamine
m-bis(4-p-aminophenyl-2-thiazolyl)benzene
m-methylenedianiline
m-phenylenediamine
m-xylylenediamine
N,N'-bis(4-aminobenzyl)-p-phenylenediamine
p-phenylene diamine
p-xylylenediamine
toluenediamine Usable diamines having ether linkages are listed in U.S. Pat. No. 4,460,783, col. 2, lines 25–63, the content of which is incorporated herein by reference.

As the ethylenically unsaturated dicarboxylic acid anhydride, there can be used at least one of maleic anhydride, citraconic anhydride, itaconic anhydride, pyrocinchonic anhydride, dichlormaleic anhydride and the like.

The flame-retardant bisimide compositions of the invention are used to form curable flame-retardant resin compositions. The curable flame retardant resin compositions may be used as varnishes, molding materials, impregnating resins and the like and either directly cured to a thermoset structure, preferably, first partially reacted, e.g. by chain extending polymerization, before curing at temperatures on the order of 100°–300° C., e.g. 200°–250° C., to form thermoset, flame resistant products having excellent flexibility and heat resistance. Such curable resin compositions are typically formed by adding to the flame retardant bisimide compositions, one or more coreactant resins or compounds such as chain extender, catalyst such as dicyandiamide, unsaturated polyester, vinyl ester resin, polyamine, epoxide, phenolic resin, imidazole and the like. Specific forms of the foregoing compositions usable with the bisimide compositions of the invention are defined in the aforementioned U.S. Pat. No. 4,460,783, col. 4, line 13 through col. 6, line 49, the content of which is incorporated herein by reference. When used to prepare laminates for the electrical industry, these resin compositions are polymerized in an organic solvent at elevated temperature, optionally in the presence of a free radical initiator, to form an advanced polymeric composition which is then used in conventional manner to prepare the laminates as more particularly described in U.S. Pat. No. 5,004,775, cols. 5 and 6, the content of which is also incorporated herein by reference.

Exemplary of the invention are the following specific Examples wherein parts and percentages are by weight unless otherwise indicated.

EXAMPLE 1

Preparation of Bisamic Acid Intermediate with Mixed End Groups

To a reaction vessel were added with stirring 14.5 moles of toluene, 0.4 mole dimethyl acetamide, 2.01 moles of maleic anhydride ("MA") and 0.23 mole of tetrabromophthalic anhydride ("TBPA") (0.114 mole ratio TBPA/MA). This preferred ring-halogenated (brominated) compound having four bromine atoms per aromatic ring was obtained from Great Lakes Chemical Corp. as PHT-4. To a separate vessel was added with stirring 14.5 moles of toluene and 1.12 moles of a diamine as bis-aminophenoxyphenyl propane, ("BAPP"), more particularly identified as 4,4'-[(1-methylethylidene) -bis-(4,1-phenylalkoxy)]-bis-benzenamine and having the following structural formula:

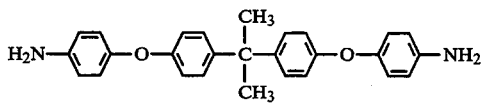

Slow addition with stirring over a period of 30–40 minutes of the BAPP solution to the first solution formed a bisamic acid intermediate mixture in the form of a slurry of the solid reaction product suspended in the liquid solvent. The component of the mixture responsible for the (subsequent) flame retardant property was a mixed bisamic acid intermediate compound having brominated phthalamide and maleamide end groups of the formula:

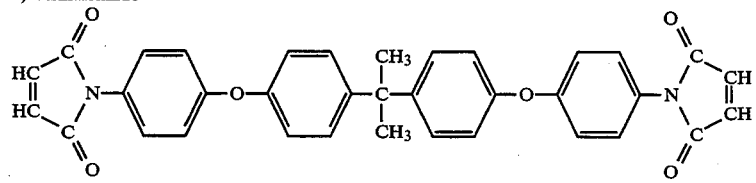

Because of the excess MA as compared to TBPA, the major component of the mixture was the bisamic acid intermediate with maleamide groups on each end of the molecules. Also formed, albeit in very small quantity due to the aforementioned excess of MA, was the bisamic intermediate compound with tetrabromophthalamide groups on each end of the molecule.

EXAMPLE 2

Preparation of Flame Retardant Bisimide Composition

This shows ring-closing dehydration of the intermediate bisamic acid mixture of Example 1.

To the slurry of Example 1 was added (with stirring) 0.15 mole of methane sulfonic acid and then the reactor contents were heated to reflux (about 113° C.). Over a period of about seven hours, water of reaction and about 50% of the toluene was distilled off and the reaction product gradually dissolved in the remaining toluene, dimethyl acetamide mixture. The reaction solution was then cooled to 5°–10° C. to initiate crystallization of the reaction product. The solid reaction product was filtered, washed and dried. Analysis using High Performance Liquid Chromatography showed a 99+% mixture of three components—i.e. bismaleimide, bisphthalimide and mixed maleimide/phthalimide with about 1% residual bisamic acid. From the ratios of reactants used, the major component was assumed to be the bismaleimide and the lesser component the mixed maleimide/phthalimide. Such mixture, constituting an embodiment of the flame retardant bisimide composition of the invention had the following formula:

a) Mixed Bisimide - i.e. Mixed Maleimide/Phthalimide

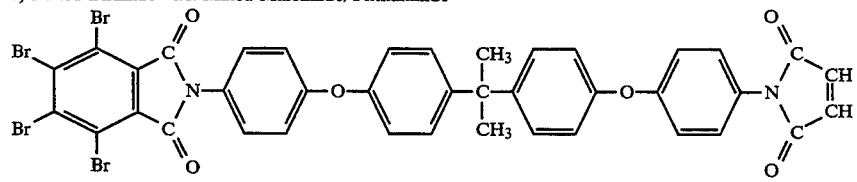

and b) Bismaleimide

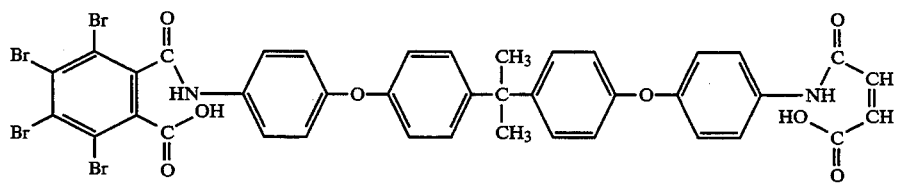

The bromine content of the composition is in Table 1 following; theoretical bromine contents are assumed equal. To verify that the mixed bisimide component was formed, a control reaction was run without MA—i.e. only diamine (BAPP) and TBPA were used with the amount of TBPA at 0.21 mole equal to twice the molar quantity of BAPP used. Upon addition of the diamine solution to the TBPA solution, a precipitate formed which was necessarily the bisamic acid intermediate having all brominated phthalamide end groups. Further reaction of this intermediate in the presence of acid catalyst did evolve water which showed that ring closure had occurred.

The above procedures of Example 1 and this Example 2 were repeated except using 4-bromo-1,8 naphthalic anhydride ("BNA") as the flame retardant ("FR") instead of TBPA at a mole ratio of FR/MA in the initial reaction (in order to obtain an equivalent halogen level as in Example 1) of 0.85:1.

EXAMPLE 3

Preparation of Chain Extended Flame Retardant Compositions

This shows chain extension of the flame retardant bisimide compositions which are capable of curing to a thermoset condition.

390.2 gm of the flame retardant bisimide compositions of Example 2 were dissolved in 2.57 moles of dimethyl formamide, 0.10 mole N-methyl pyrrolidinone to which was added 0.10 mole dicyandiamide. The solutions were heated with stirring to about 100°–120°

C. at which point 0.004 mole dimethylaminopyridine was added. The solutions were held at 100°–120° C. until the desired degree of reaction was reached. This was determined by sampling the mixture and determining gel time by the stroke cure method on a cure plate. When the chain extended resin product had a gel time of about 4–6 minutes at 171° C., the resin solutions were cooled, filtered and stored at 2° C. for future use in laminate preparation.

EXAMPLES 4–9

This shows preparation of laminates for use as printed wiring boards using the chain extended compositions of Example 3.

Laminate preparation was carried out in three steps. In the first step, fiberglass cloth (Clark-Schwebel brand with a CS-309 chemical finish) was impregnated in a drip pan with the flame retardant compositions of Example 3 to form B-staged prepreg sheets. The coated fiberglass cloth was drawn through nip rolls separated by shims to form an adjustable gap, the opening of which controlled the resin content of the impregnated sheet. The wet sheet was hung in an oven at 160° to 210° C. for 3 to 10 min.

In the second step, sheets of the B-staged prepreg of the first step were cut into sections of 6 in.×12 in. (15 cm×30 cm) and laid atop each other. The stack was placed between two sheets of 1 oz. (28.3 g) Gould brand JTC Poly copper foil. This assembly was then placed between two 0.083 in. (0.211 cm) thick steel plates which in turn were placed between two pieces of ordinary box cardboard. The entire construction was placed between preheated platens of a press at 177° C. and pressed for 2.5 hours at 250 psi (1722 kPa). The platens were then cooled to 50° C. and the laminates removed from the press. The results of this lamination and pressing step were non post-cured laminates.

In the third step, the non-post-cured laminates were post-cured for 16 hours at 220° C. in an air circulating oven to fully crosslink the system and develop the final properties in the laminates.

The finished laminates were flat and showed no blistering (bubbling) or lifting of the copper foil. The laminates were then cut into ten 6 inch by 0.5 inch (15×1.2 cm) strips and soaked in dilute nitric acid for 15 to 30 min. to remove (etch) the copper from the surfaces of the laminates. When etching was complete the laminate strips were washed with deionized water and allowed to dry. The strips were then tested for flame resistance according to the aforementioned Underwriters Laboratories UL 94 protocol. Results are in Table 1 following.

EXAMPLE 10

This control example compares performance of the reactive flame retardant additive of the system of Example 1 of U.S. Pat. No. 4,876,325 with that of Examples 1–9 above (except dicyandiamide was not used since having no effect on flame retardant performance).

425 gms. of pure bismaleimide resin as Skybond S-3030 from Monsanto Company which contained no flame retardant of any type was added to a flask along with 3.1 moles of dimethyl formamide. The mixture was stirred at 100° C. until the bismaleimide completely dissolved. To another reaction flask was added 1.8 moles of styrene-terminated brominated bisphenol A defined as component (b) in U.S. Pat. No. 4,876,325. The amount used was (theoretically) adequate to provide 10% Br in the reaction product with the bismaleimide. This mixture was stirred at 50° C. until the bisphenol component was completely dissolved.

The bisphenol solution, maintained at 50° C., was added to the bismaleimide solution over 6 hours, while the latter was maintained at 100° C. with agitation. The reaction proceeded until the desired extent of reaction was attained. The bismaleimide composition thus produced was stored at 2° C. until lamination using this solution took place.

Lamination followed the procedure in Examples 4–9 above. The non-post-cured/pressed laminate had no blistering or lifting of the copper foil. However, post-curing in the circulating air oven generated a tremendous amount of volatiles causing blistering and lifting of the copper foil over 50% of the surface of the laminate. The volatiles also caused a fire during post-curing as evidenced by a thick layer of soot formed on the surface of the copper. This laminate underwent severe delamination and was considered a failure.

The preceding description is for illustration only and is not to be taken in a limited sense. Various modifications and alterations will be readily suggested to persons skilled in the art. It is intended, therefore, that the foregoing be considered as exemplary only and that the scope of the invention be ascertained from the following claims.

I claim:

1. A mixed bisimide compound having the formula:

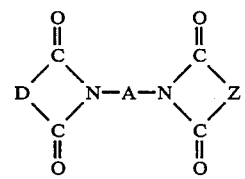

where D is a divalent radical containing a polymerizable carbon-carbon double bond, A is an organic divalent linking group and Z is a halogenated divalent radical containing one or more aromatic or bicyclo groups.

2. The mixed bisimide of claim 1 wherein:

TABLE 1

| Ex. | FR Type | Bromine Content Theoretical[1] | Number Of Laminate Plies | Resin Content Wt. % | Laminate Thickness (cm) | Laminate UL-94 Rating | Fiber-Glass Type |
|---|---|---|---|---|---|---|---|
| 4 | TBPA | 2.56 | 2 | 35.8 | 0.038 | <V-2 | 7628 |
| 5 | TBPA | 5.0 | 2 | 37.5 | 0.038 | V-1 | 7628 |
| 6 | TBPA | 7.5 | 2 | 26.0 | 0.033 | V-0 | 7628 |
| 7 | TBPA | 7.5 | 20 | 69.0 | 0.165 | V-1 | 1080 |
| 8 | TBPA | 10.0 | 20 | 65.0 | 0.150 | V-0 | 1080 |
| 9 | BNA | 10.0 | 20 | 67.7 | 0.216 | V-0 | 1080 |

[1]Of the mixed bisimide of the flame retardant composition before laminating.

D is:
where $R_1$ and $R_2$ are each H;
A is:
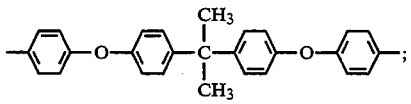
and
Z is:
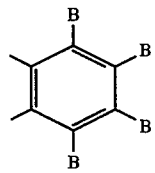
where B is Br or Cl.